(12) United States Patent
Abe (10) Patent No.: US 7,018,796 B2
(45) Date of Patent: Mar. 28, 2006

(54) PREINCUBATION ASSAY METHODS

(75) Inventor: Kenji Abe, Settsu (JP)

(73) Assignee: Shionogi & Co., Ltd., Osaka (JP)

( * ) Notice: Subject to any disclaimer, the term of this patent is extended or adjusted under 35 U.S.C. 154(b) by 163 days.

(21) Appl. No.: 10/149,153

(22) PCT Filed: Mar. 29, 2001

(86) PCT No.: PCT/JP01/02619

§ 371 (c)(1),
(2), (4) Date: Jun. 10, 2002

(87) PCT Pub. No.: WO01/77371

PCT Pub. Date: Oct. 18, 2001

(65) Prior Publication Data

US 2003/0044824 A1    Mar. 6, 2003

(30) Foreign Application Priority Data

Apr. 7, 2000   (JP)   ............................. 2000-105887

(51) Int. Cl.
*C12Q 1/68* (2006.01)
(52) U.S. Cl. .................... 435/6; 435/91.2; 436/501
(58) Field of Classification Search .................... 435/6, 435/91.2; 436/501
See application file for complete search history.

(56) References Cited

U.S. PATENT DOCUMENTS

| | | | | |
|---|---|---|---|---|
| 5,264,343 A | * | 11/1993 | Krystosek et al. | ............. 435/6 |
| 5,652,210 A | * | 7/1997 | Barr et al. | ..................... 514/2 |
| 6,107,073 A | * | 8/2000 | Chen | ......................... 435/194 |

FOREIGN PATENT DOCUMENTS

| | | | |
|---|---|---|---|
| JP | 3-297398 | | 12/1991 |
| WO | 91/4338 | | 4/1991 |
| WO | WO 96/37619 | | 11/1996 |
| WO | 97/7670 | | 3/1997 |
| WO | WO 97/12033 | * | 4/1997 |
| WO | WO 99-51781 | | 10/1999 |
| WO | 00/06529 | | 2/2000 |

OTHER PUBLICATIONS

Ishii et al (Hepatology (1999) 29(4):1227-1235).*
Webster's New Riverside dictionary, p. 1009 (1994).*
Davis et al (Antiviral Research (1996) 30:133-145).*
Horton et al (Biotechniques (1998) 24(3):420-422).*

* cited by examiner

*Primary Examiner*—Jeffrey Fredman
(74) *Attorney, Agent, or Firm*—Wenderoth, Lind & Ponack, L.L.P.

(57) ABSTRACT

Pseudo-positive data can be reduced by incubating a solution containing an enzyme in the absence of a test substance and a substrate of the enzyme.

3 Claims, 5 Drawing Sheets

PREINCUBATION ASSAY METHODS

This application is a 371 of PCT/JP01/02619 filed Mar. 29, 2001.

TECHNICAL FIELD

The present invention relates to a method for an assay of an activator or an inhibitor to an enzyme, specially a polymerase, a RNA polymerase and a RNA-dependent RNA polymerase.

BACKGROUND ART

A method for an assay of an activator or an inhibitor to an enzyme generally comprises mixing the enzyme, a substrate of the enzyme, anything essential to an enzyme reaction such as a metal ion and a test substance, reacting the mixture under a condition where the enzyme reaction can be carried out such as a buffer condition, a reaction temperature or the like, measuring or calculating an enzyme activity by any means and comparing it with an enzyme activity in the absence of a test substance.

For example, an assay of an activator or an inhibitor to a polymerase can be carried out as follows. First, a polymerase, a labeled substrate, a template, a primer, a metal ion and a test substance are mixed at the same time or in order for the polymerase reaction. The labeled substrate is incorporated to a reaction product, which is known as an incorporation. After reaction, an amount of the labeled substrate incorporated to the reaction product is measured. An enzyme activity calculated on the basis of the above measured amount is compared with that in the absence of a test substance.

Even if a result of the above assay suggests that a test substance may possess an activity or inhibitory activity to an enzyme, the activity may be pseudo-positive due to nonspecifically acting or binding to the enzyme based on the structure or character of the test substance. Therefore, in order to prove the result of the assay to be positive, it is necessary to confirm that the test substance is really an activator or an inhibitor to an enzyme by the other assay. However, the other assay with a complicated process may not be suitable for the first assay.

Recently, a high throughput screening (referred to as HTS) is very important on the early stage of the development of medicine. HTS enables several hundreds to ten thousands compounds to be assayed at the same time, but causes a problem of how to analyze an enormous number of data.

Journal of General Virology (2000), 81, 759–767 discloses that a pre-incubation of HCV RNA-dependent RNA polymerase in the presence of a template and a primer enhances an enzyme activity, without mentioning an assay of an activator or an inhibitor to an enzyme at all. The above document only discloses a character of the enzyme.

It is important to obtain useful information from data obtained by HTS without pseudo-positive data. A method for an assay of an activator or an inhibitor to an enzyme with no or little pseudo-positive data has been desired.

DISCLOSURE OF INVENTION

The present inventor found a method for an assay of an activator or an inhibitor to an enzyme, wherein pseudo-positive data can be reduced by a pre-incubation, which comprises incubating a solution containing said enzyme in the absence of a test substance and a substrate of said enzyme.

The present invention provides the following inventions.
(1) A method for an assay of an activator or an inhibitor to an enzyme which comprises incubating a solution containing said enzyme in the absence of a test substance and a substrate of said enzyme.
(2) The method for an assay of an activator or an inhibitor to an enzyme according to the above (1) which comprises:
  (a) incubating a solution containing said enzyme in the absence of a test substance and a substrate of said enzyme, and
  (b) comparing an enzyme activity measured by mixing a test substance and a substrate of said enzyme with said solution incubated and reacting said enzyme with said substrate of said enzyme with an enzyme activity measured by mixing only a substrate of said enzyme with said solution incubated and reacting said enzyme with said substrate of said enzyme.
(3) The method for an assay according to the above (1) or (2) which comprises incubating said solution for 0.5 hours or more.
(4) The method for an assay according to any one of the above (1) to (3) which comprises incubating said solution at 20 to 40° C.
(5) The method for an assay according to any one of the above (1) to (4) wherein said enzyme is of a virus.
(6) The method for an assay according to any one of the above (1) to (5) wherein said enzyme is a polymerase.
(7) The method for an assay according to any one of the above (1) to (6) wherein said solution contains a polymerase, a template, a primer and a metal ion.
(8) A method for activating or inhibiting an enzyme which comprises contacting said enzyme with a compound obtained by the method for an assay according to any one of the above (1) to (7).
(9) A method for activating or inhibiting replication of a virus which comprises contacting said virus with a compound obtained by the method for an assay according to the above (5).
(10) A compound which is obtained by the method for an assay according to any one of the above (1) to (7).
(11) A pharmaceutical composition for activating or inhibiting an enzyme which comprises as an active ingredient a compound obtained by the method for an assay according to any one of the above (1) to (7).
(12) A method for an assay of an inhibitor to a virus RNA-dependent RNA polymerase which comprises incubating a solution containing said polymerase, a template RNA, a primer RNA and a metal ion in the absence of a test substance and a substrate RNA of said polymerase.
(13) A method for an assay of an inhibitor to a virus RNA-dependent RNA polymerase according to the above (12) which comprises:
  (a) incubating a solution containing said polymerase, a template RNA, a primer RNA and a metal ion in the absence of a test substance and a substrate RNA of said polymerase, and
  (b) comparing a virus RNA-dependent RNA polymerase activity measured by mixing a test substance and a substrate RNA of said polymerase with said solution incubated and reacting said polymerase with said substrate of said polymerase with a virus RNA-dependent RNA polymerase activity measured by mixing only a substrate RNA of said polymerase with said solution incubated and reacting said polymerase with said substrate of said polymerase.

(14) The method for an assay according to the above (12) or (13) which comprises incubating said solution for 0.5 hours or more.
(15) The method for an assay according to any one of the above (12) to (14) which comprises incubating said solution at 20 to 40° C.
(16) The method for an assay according to any one of the above (12) to (15) wherein said template RNA is poly(A), said primer RNA is oligo(U), said metal ion is $Mg^{2+}$ and said substrate RNA is $^3$H-UTP or $^{32}$P-UTP.
(17) A method for inhibiting a virus RNA-dependent RNA polymerase which comprises contacting said virus RNA-dependent RNA polymerase with a compound which is obtained by the method for an assay according to any one of the above (12) to (16).
(18) A method for inhibiting replication of a virus which comprises contacting said virus with a compound obtained by the method for an assay according to any one of the above (12) to (16).
(19) The method according to any one of the above (12) to (18) wherein said virus belongs to Hepacivirus genus.
(20) The method according to any one of the above (12) to (18) wherein said virus is an HCV.
(21) A compound of the formula: A—C(=O)—CH=C(OH)—COOH wherein A is an organic residue, which is obtained by the method for an assay according to any one of the above (12) to (16), (19) and (20).
(22). A pharmaceutical composition for treating hepatitis C which comprises as an active ingredient a compound obtained by the method for an assay according to any one of the above (12) to (16), (19) and (20).
(23) A pharmaceutical composition for treating hepatitis C which comprises as an active ingredient a compound of the formula: A—C(=O)—CH=C(OH)—COOH wherein A is an organic residue, which is obtained by the method for an assay according to any one of the above (12) to (16), (19) and (20).

The present invention is explained in detail below.

The present invention relates to a method for an assay of an activator or an inhibitor of an enzyme. In the present specification, an assay of an activator or an inhibitor to an enzyme includes the first assay which evaluates test substances that are unknown to be an activator or an inhibitor of an enzyme and the revaluation assay which evaluates test substances that are known to be an activator or an inhibitor of an enzyme. The assay of the present invention can be used for all kinds of assay. For example, the present assay can be used for an identification of an activator or an inhibitor to a polymerase, an inhibitor to a virus polymerase, an inhibitor to RNA-dependent RNA polymerase or an inhibitor to HCV RNA-dependent RNA polymerase.

The present invention is used for an assay of an activator or an inhibitor to an enzyme and characterized in that an incubation is carried out before an enzyme reaction, in detail, that an incubation of a solution containing said enzyme in the absence of a test substance and a substrate of said enzyme. In the present specification, the above incubation is also expressed as a pre-incubation. In detail, the present invention includes incubating a solution containing an enzyme in the absence of a test substance and a substrate of the enzyme at a temperature where an effect of a pre-incubation can be exhibited for an incubation time where an effect of a pre-incubation can be exhibited.

A temperature where an effect of a pre-incubation can be exhibited is, for example, approximately 15° C. to 50° C., preferably 20° C. to 40° C., and more preferably 20° C. to 30° C.

An incubation time where an effect of a pre-incubation can be exhibited is approximately 15 minutes or more, preferably 0.5 hour or more, more preferably 1 hour or more. For example, preferred is approximately 15 minutes to 12 hours, 0.5 to 3 hours, 0.5 to 2 hours, especially 1 hour.

An incubation of a solution containing an enzyme in the absence of a test substance and a substrate of the enzyme seems to form a condition where an enzyme reaction can easily be preformed.

The term "the absence of a test substance and a substrate of an enzyme" includes a condition where a test substance and a substrate of an enzyme are not included. A solution containing said enzyme may be incubated together with anything essential to an enzyme reaction except a substrate of an enzyme.

The term "a solution containing an enzyme" includes a solution containing at least an enzyme, preferably a solution containing an enzyme and anything essential to an enzyme reaction except a substrate of an enzyme.

Anything essential to an enzyme reaction except a substrate of an enzyme includes, depending on the enzyme to be used, for example, high molecular weight compounds, low molecular weight compounds, metal ions, halogenous ions, amino acids, polypeptides, nucleic acids, polynucleotides or the like.

The assay of the present invention is useful for an assay of an activator or an inhibitor of a polymerase, specially an assay relating to a nucleic acid elongation reaction in the presence of a primer. When an enzyme is a polymerase, a solution preferably contains a polymerase, a template, a primer and a metal ion.

A template includes a template DNA or a template RNA, for example, a homopolymer such as a synthesized homopolymer, poly(dA), poly(dT), poly(dG), poly(dC), poly(A), poly(U), poly(G), poly(C) or the like or a heteropolymer such as a natural type of nucleic acid polymer, a synthesized heteropolymer or the like. A length of a template is not limited and can be selected depending on a kind of an enzyme. For example, a template of approximately 8 to 1000 bases, 50 to 800 bases, 100 to 500 bases can be used. A commercially available template or the like may be used.

A primer includes a primer DNA or a primer RNA. A primer complementary to a template can be used. When a template is a homopolymer, a primer such as oligo(dA), oligo(dT), oligo(dG), oligo(dC), oligo(A), oligo(U), oligo(G), oligo(C) or the like can be used. When a template is homopolymer, a primer partially complementary to a template can be used. A length of a primer depends on a kind of an enzyme. A primer of 12 to 18 bases can generally be used.

A metal ion includes $Mg^{2+}$, $Mn^{2+}$, $Na^+$, $K^+$ or the like. $Mg^{2+}$ is generally essential to a polymerase.

A test substance includes a substance used for an assay, for example, a protein such as a polypeptide as well as a low molecular weight compound.

An enzyme reaction after a pre-incubation starts by adding a substrate of the enzyme to a solution containing the enzyme. The prior method described in The EMBO Journal vol.15, no.1, pp12–22, 1996 requires an enzyme reaction temperature of approximately 22° C. An enzyme loses an activity of itself over such a temperature and does not work below the temperature. The pre-incubation assay method is different from the prior method and an enzyme reaction can be carried out at approximately 10 to 40° C., preferably 20 to 40° C. When a human enzyme, an enzyme of a virus infecting human being or the like is used in the assay of the present invention, a enzyme reaction can be carried out at the same temperature as a human temperature, specially 37° C. Therefore, the present invention is very useful. Further such temperature heightens an activity of an enzyme activity. As a result, the detectability of an assay increases.

An activating effect or inhibiting effect of a test substance to an enzyme can be identified by comparing an enzyme activity, which is measured by mixing a test substance and a substrate of the enzyme with a solution incubated and reacting the enzyme with the substrate of the enzyme, with an enzyme activity, which is measured by mixing only the substrate of the enzyme with a solution incubated and reacting the enzyme with the substrate of the enzyme. To a solution incubated may be added a substrate of an enzyme and an optional test substance. To a substrate of an enzyme and an optional test substance may be added a solution incubated. The addition order does not matter as far as a substrate of an enzyme contacts with an enzyme.

The term "mixing only a substrate of said enzyme" includes mixing no test substance. As far as no test substance is included, a solution may include anything other than a substrate of an enzyme. For example, a reaction solution for dissolving or suspending a substrate of an enzyme may be included. Anything may be mixed as far as data for being compared with data in the presence of a test substance can be prepared. An enzyme activity measured by mixing only a substrate of a enzyme with a non-incubated solution and reacting the enzyme with the substrate of the enzyme can be used as a reference. Preferred is an enzyme activity measured by mixing only a substrate of a enzyme with a solution incubated and reacting the enzyme with the substrate of the enzyme.

An enzyme activity can be measured by using a labeled substrate of the enzyme. When a polymerase is used, an amount of the labeled substrate of the enzyme incorporated to the reaction product can be measured. An isotope-labeled substrate of an enzyme can be used as a labeled substrate of the enzyme and a radioactivity can be measured by a scintillation counter or the like. A labeled substrate of an enzyme or the like can be separate from a reaction solution by using a commercially available filter such as a filter modified by a dimethylaminoethyl group or the like.

A low molecular weight compound includes an organic compound of molecular weight 15 to 1000. Atoms constituting such compound includes hydrogen, lithium, boron, carbon, nitrogen, oxygen, fluorine, sodium, magnesium, aluminum, sulfur, chlorine, potassium, calcium, iron, barium, bromine, iodine or the like.

A polypeptide includes not only a natural peptide but also a modified peptide such as peptide isoster or the like.

A substrate of an enzyme includes a substance on which an enzyme acts, for example, a high molecular weight compound, a low molecular weight compound, an amino acid, a polypeptide, a nucleic acid, a polynucleotide or the like. An example of a substrate of a polymerase includes dATP, dTTP, dGTP, dCTP, ATP, UTP, GTP, CTP or the like. An example of a labeled substrate of an enzyme includes $^3$H-UTP, $^{32}$P-UTP or the like.

An enzyme includes a protein catalyzing an enzyme reaction, for example, any kind of oxygenase, any kind of phosphotransferase (e.g., phosphokinase, protein kinase or the like), any kind of protease, any kind of polymerase, any kind of synthetase or the like. In the present invention, not only a full length enzyme but also a deletion mutant, a substitution mutant or an addition mutant having an enzyme activity can be used. For example, a recombinant enzyme can be used.

A polymerase includes a polynucleotide chain synthetase, for example, DNA polymerase (e.g., DNA-dependent DNA polymerase, RNA-dependent DNA polymerase) or RNA polymerase (e.g., DNA-dependent RNA polymerase, RNA-dependent RNA polymerase).

A protease includes a proteolytic enzyme, an enzyme catalyzing hydrolysis of a peptide bond. An example of a protease includes a serine protease, a cysteine protease, a metalloprotease or an aspartic protease. A protease includes an endopeptidase and an exopeptidase.

A virus is not limited to the specific virus. An example of a virus includes HIV (human immunodeficiency virus), HCV (hepatitis C virus), HBV (hepatitis B virus), HTLV (human T cell leukemia virus), influenza virus or the like. Preferred is a virus which belongs to Hepacivirus genus, especially HCV.

An enzyme of HIV includes a reverse transcriptase (a RNA-dependent DNA polymerase, a RNA-dependent DNA polymerase having a RNaseH activity), an integrase, a protease and the like. An enzyme of HCV includes a RNA-dependent RNA polymerase, protease (serine protease, metalloprotease), an helicase and the like. An enzyme of HBV includes a DNA polymerase (an enzyme having a DNA-dependent DNA polymerase activity, a RNA-dependent DNA polymerase activity and/or a RNaseH activity) and the like. An enzyme of HTLV includes a reverse transcriptase, an integrase, a protease and the like. An enzyme of influenza virus includes a RNA-dependent RNA polymerase, an endonuclease, a sialidase and the like.

Any enzyme can be used in the present invention. A protein having an enzyme activity can be used. Preferred is an enzyme relating to a long length chain of nucleic acids (e.g., an integrase, a helicase, a polymerase or the like), especially a polymerase. Preferred among polymerases is a RNA-dependent RNA polymerase (e.g., a virus RNA-dependent RNA polymerase), especially a virus RNA-dependent RNA polymerase of a flavivirus, more especially a HCV RNA-dependent RNA polymerase.

An example of a virus having a RNA-dependent RNA polymerase includes a virus which belongs to Picornaviridae, Caliciviridae, Togaviridae, Flaviviridae, Coronaviridae, Paramyxoviridae, Orthomyxoviridae, Rhabdoviridae, Arenaviridae, Bunyaviridae or the like. Preferred is a virus which belongs to Flaviviridae, especially a virus which belongs to Flaviviridae family Hepacivirus genus.

An example of a virus which belongs to Flaviviridae family includes a hepatitis C virus, a yellow fever virus, a dengue virus, a Japanese/encephalitis virus, a West Nile fever virus, a St. Louis encephalitis virus, a Rocio encephalitis virus, a Murray Valley encephalitis virus, or the like. These viruses have a RNA-dependent RNA polymerase. Since these viruses relate to diseases of a mammal including human being, it is important to find inhibitors of these virus RNA-dependent RNA polymerase.

An enzyme includes not only an enzyme having one enzyme activity, but also an enzyme having two or more enzyme activities. For example, a example of an enzyme having two or more enzyme activities includes a HBV DNA polymerase (an enzyme having a DNA-dependent DNA polymerase activity, a RNA-dependent DNA polymerase activity and/or a RNaseH activity) or the like.

When a HIV reverse transcriptase (an enzyme having a RNA-dependent DNA polymerase activity and a RNaseH activity) is used, not only a part having each enzyme activity but also a part having both enzyme activities can be used for the present invention.

There are many genotypes of HCV. In the present invention, an enzyme of any genotype of HCV can be used. An example of genotype of HCV includes genotype 1a, genotype 1b, genotype 2a, genotype 2b, genotype 3, genotype 4 or the like.

HCV RNA-dependent RNA polymerase is encoded in the NS5B (nonstructural protein 5B) region of HCV. In the present invention, any enzyme having a RNA-dependent RNA polymerase activity can be used. For example, an enzyme having a RNA-dependent RNA polymerase activity encoded in NS5B of the above genotype of HCV (e.g., genotype 1a, genotype 1b, genotype 2a, genotype 2b, genotype 3, genotype 4).

An activator includes a substance activating an enzyme reaction.

An inhibitor includes a substance inhibiting an enzyme reaction. Preferred is an inhibitor having $IC_{50}$ of 100 µM or less, specially 10 µM or less, more specially 1 µM or less.

The present invention relates to a pre-incubation assay method and is useful for an assay of an enormous number of compounds, especially a high throughput assay (HTS). The present invention enables pseudo-positive data to be reduced and lead compounds can efficiently be selected.

An enzyme can be activated or inhibited by contacting a substance obtained by the assay of the present invention with an enzyme. A replication of a virus can be activated or inhibited by contacting a substance obtained by the assay of the present invention with a virus.

BEST MODE FOR CARRYING OUT THE INVENTION

A pre-incubation assay method of the present invention is explained below, compared with a prior method. Though it is explained by using HCV RNA-dependent RNA polymerase, one of polymerase as an example of an enzyme, an enzyme is not limited to such polymerase. Any kind of an enzyme can be used in the present invention. Preferred is a polymerase, specially a RNA polymerase, especially RNA-dependent RNA polymerase, more especially HCV RNA-dependent RNA polymerase.

Prior Method

A HCV RNA-dependent RNA polymerase, template RNA, primer RNA, substrate RNA, Mg ion ($Mg^{2+}$) and a test substance are mixed at the same time to start an enzyme reaction and measure an enzyme activity. It can be known whether a test substance activates or inhibits an activity of a HCV RNA-dependent RNA polymerase by comparing the above value of an enzyme activity with that measured in the absence of a test substance. $IC_{50}$ value can be used, which is a concentration of a test substance able to inhibit 50% of an enzyme activity. For example, one of prior methods can be carried out in accordance with the later described Reference 1.

Pre-incubation Assay Method

A HCV RNA-dependent RNA polymerase, template RNA, primer RNA and Mg ion ($Mg^{2+}$) are pre-incubated at approximately 25° C. for approximately 1 hour. After that, substrate RNA and a test substance are added to start an enzyme reaction and measure an enzyme activity. $IC_{50}$ value can be calculated by comparing with an enzyme activity measured in the absence of a test substance as well as the above prior method. An inhibitor can be selected by comparing $IC_{50}$. An example of a procedure of this method is shown in the later described Example 1.

A pre-incubation assay method of the present invention is superior to a prior method in the following points.

1) Higher Enzyme Activity

Figure 1:
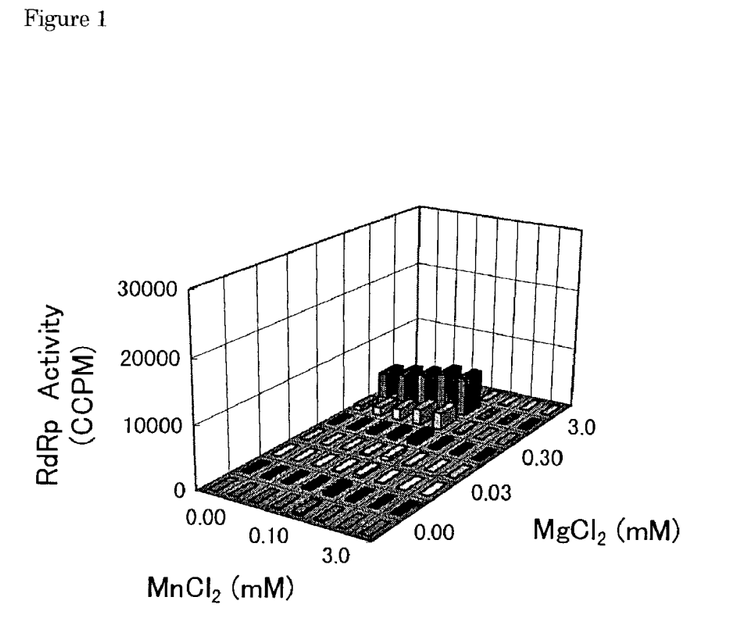
FIG. 1 shows an enzyme activity of HCV RNA-dependent RNA polymerase measured by the prior method.
Figure 2:
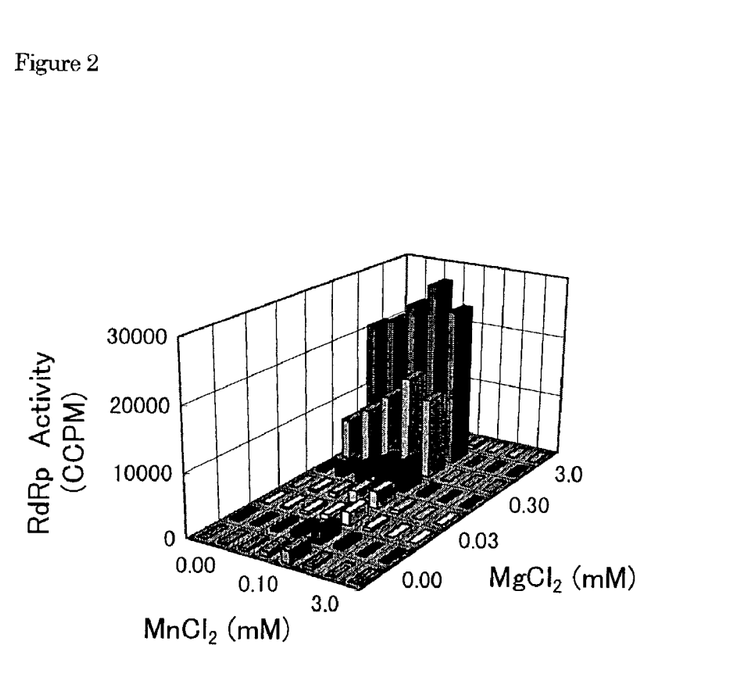
FIG. 2 shows an enzyme activity of HCV RNA-dependent RNA polymerase measured by the pre-incubation assay method.

FIGS. 1 and 2 shows charts of enzyme activities at each concentration of $Mg^{2+}$ and $Mn^{2+}$ in a prior method and a pre-incubation assay method. When a concentration of $Mg^{2+}$ is 3 mM and a concentration of $Mn^{2+}$ is 0.1 mM, an enzyme activity is 29,095 ccpm in a pre-incubation assay method whereas that is 6,288 ccpm in a prior method. An enzyme activity is 4 to 5 times as high as that in a prior method. Therefore, assay results can easily be detected and experimental errors decrease. It is useful for screening inhibitors.

Figure 3:
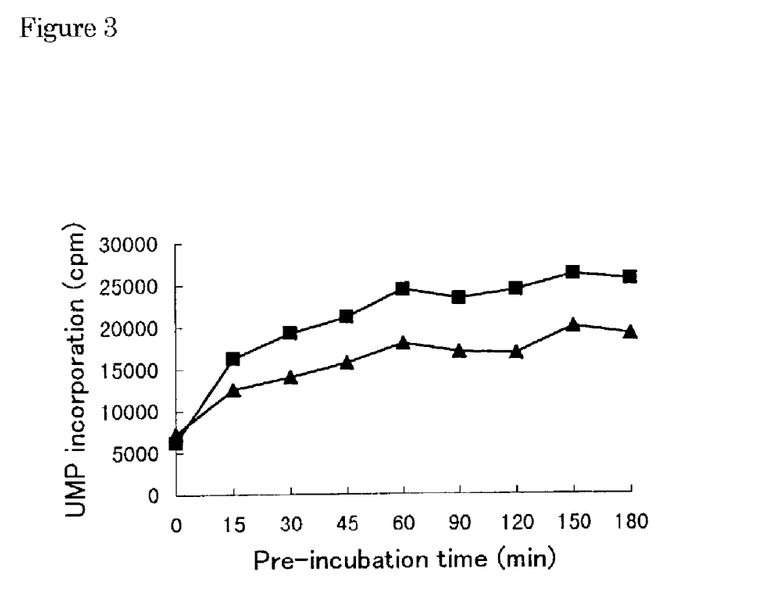
FIG. 3 shows a relationship between pre-incubation time and an enzyme activity of HCV RNA-dependent RNA polymerase when an enzyme reaction time is 30 minutes. In the figure, ■ is used when a solvent dissolving a test substance is DMSO and ▲ is used when the solvent is water.

A relationship between a pre-incubation time and an enzyme activity was examined. An example of a procedure is described in Examination 1. An enzyme activity is represented by an amount of an incorporation of uridine monophosphate (UMP) to a reaction product. A result is shown in FIG. 3. An enzyme activity gradually gets higher until a pre-incubation time is approximately 60 minutes. The difference of enzyme activities between a prior method and a pre-incubation assay method gradually gets larger. An enzyme activity measured after pre-incubating for approximately 60 minutes is approximately 4 times as high as that measured by a prior method. When a pre-incubation time is more than 60 minutes, an enzyme activity is the same as that measured after pre-incubating for approximately 60 minutes. This results shows that a preferable pre-incubation time is approximately 60 minutes.

2) Higher Thermostability

Figure 4:
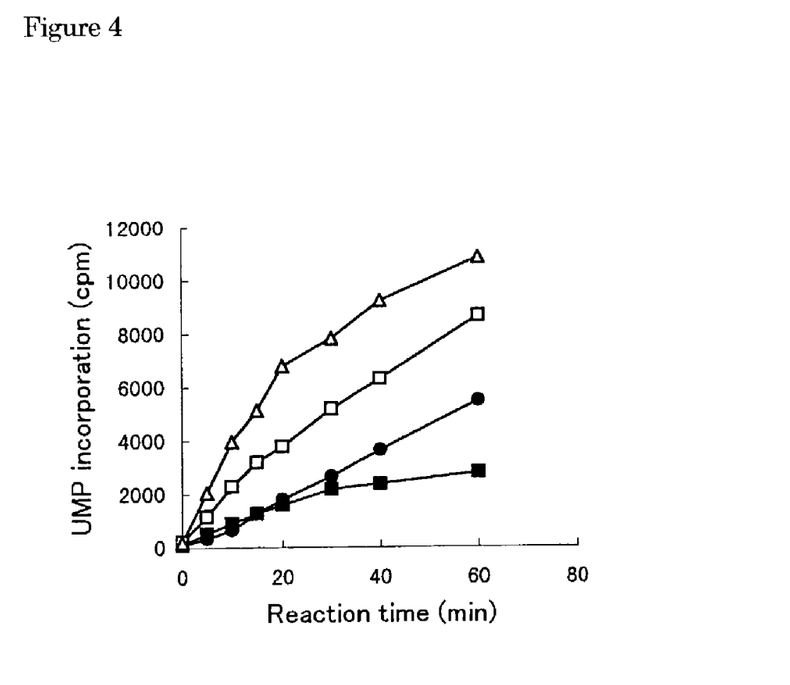
FIG. 4 shows a relationship between the presence or the absence of a pre-incubation and an enzyme reaction temperature. In the figure, each symbol represents a relationship between an incorporation of UMP by HCV RNA-dependent RNA polymerase and an enzyme reaction time. ∆ is used when an enzyme reaction after a pre-incubation is carried out at 37° C., □ is used when an enzyme reaction after a pre-incubation is carried out at 25° C., ● is used when an enzyme reaction is carried out at 25° C. without a pre-incubation and ■ is used when an enzyme reaction is carried out at 37° C. without a pre-incubation.

A relationship between the presence or absence of a pre-incubation and an enzyme reaction temperature is examined and shown in FIG. 4. In a prior method, when an enzyme reaction temperature is approximately 37° C., a longer reaction time deactivates an enzyme. Therefore, an accurate enzyme activity can not be measured and an enzyme reaction must be carried out at approximately 25° C. in a prior method. On the other hand, an enzyme reaction in a pre-incubation method proceeds well at approximately 37° C. and an assay can be carried out at a temperature more close to that of a mammal. An enzyme activity at approximately 37° C. is higher than that at approximately 25° C. Therefore, a pre-incubation method enables an assay to be carried at approximately 37° C., which is close to a temperature of a mammal.

3) Reducing Pseudo-positive Data

A pre-incubation method enable to pseudo-positive data to decrease. It is explained by using FIG. 5.

Figure 5:
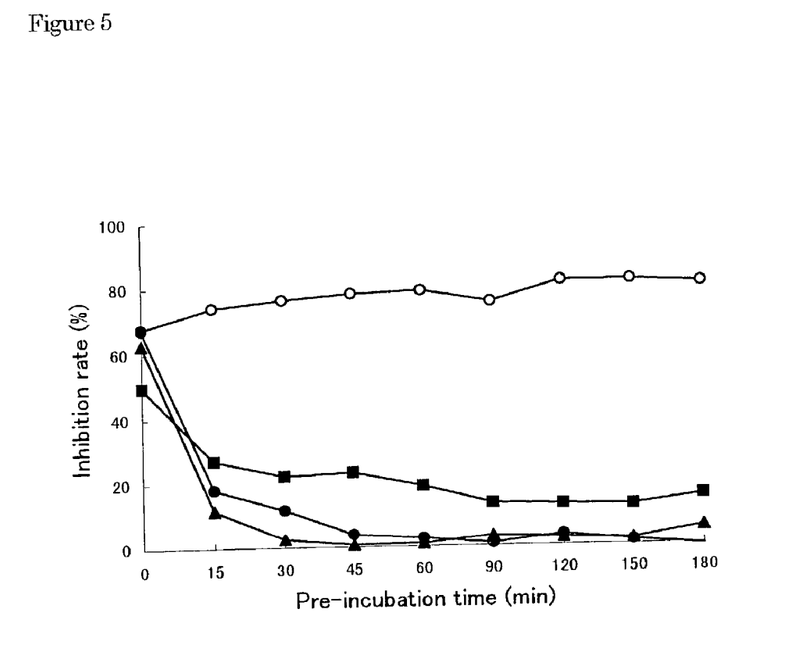
FIG. 5 shows a relationship between a pre-incubation time and each inhibitory activity of 3'-dUTP, Compound A, Compound B and Compound C to HCV RNA-dependent RNA polymerase. In the figure, ○ is used when a test substance is 3'-dUTP, ■ is used when a test substance is Compound A, ▼ is used when a test substance is Compound B and ● is used when a test substance is Compound C.

In FIG. 5, 3'-deoxyuridine triphosphate (3'-dUTP) is used as a competitive inhibitor. 3'-dUTP is incorporated as a substrate, stops the elongation of a RNA chain and can inhibit an activity of a HCV RNA-dependent RNA polymerase. Compound A, B and C show positive data in a prior method. These compounds (3'-dUTP (0.7 μM), Compound A (100 μg/ml), Compound B (50 μ/ml) or Compound C (25 μ/ml)) inhibit an activity of a HCV RNA-dependent RNA polymerase at approximately 50 to 70% of an inhibition in a prior method which is not accompanied with a pre-incubation. The structures of Compound A, B and C are shown below.

Compound A

Compound B

-continued

Compound C

When these four compounds are assayed in a pre-incubation assay method, an enzyme inhibition rate of Compound A, B and C are under 15%, whereas an enzyme inhibition rate of a positive control compound (3'-dUTP) does not change. Compound A, B and C are judged to be negative compounds.

Compounds which show positive data in a prior method in spite of no inhibition activity to a HCV RNA-dependent RNA polymerase are judged to be negative compounds in a pre-incubation assay.

This is important in a search for an inhibitor to an enzyme which can not be examined by the other method. Specially, it is important in a search for an inhibitor to a HCV RNA-dependent RNA polymerase because there is no HCV infection experiment. It can be judged by a pre-incubation of the present invention whether it is a real inhibitor or not.

Figure 9:
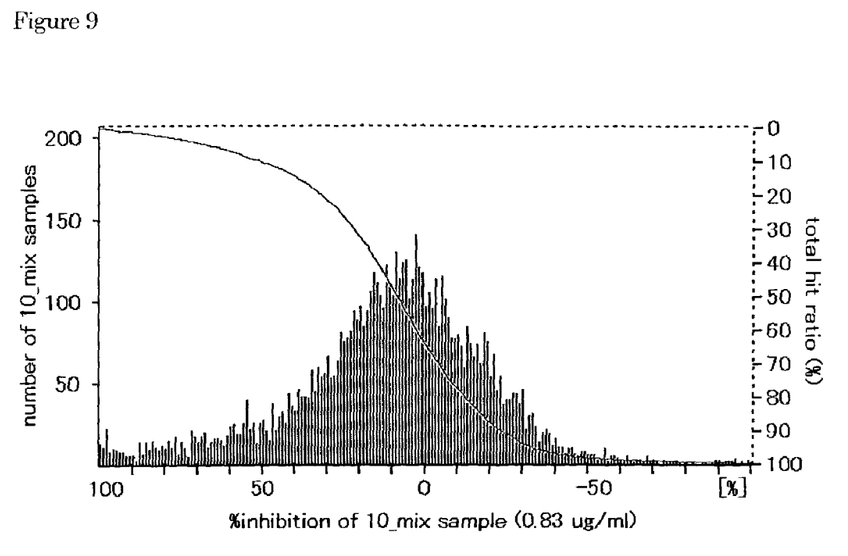
FIG. 9 shows a result of random screening carried out through the prior method.
Figure 10:
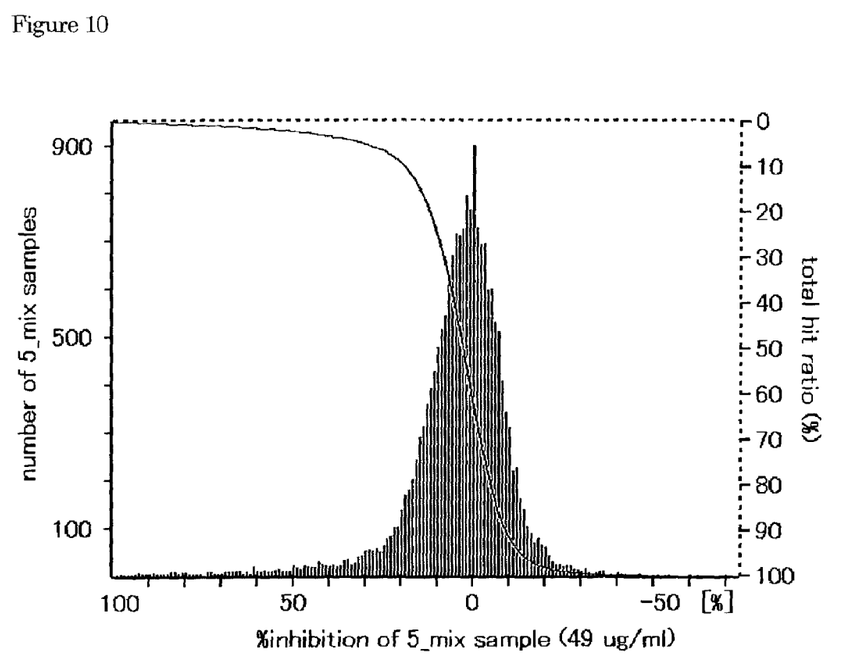
FIG. 10 shows a result of random screening carried out through the pre-incubation method.

It is specially important in a random screening wherein a large amount of compounds are examined at the same time. FIG. 9 shows a result of a random screening in a prior method. FIG. 10 shows a result of a random screening in a pre-incubation method. A bar chart shows numbers of samples at each inhibition rate (left vertical axis: a number of samples, horizontal axis: an inhibition rate). Right vertical axis shows percentages of positive compounds to the total number of all assayed compounds. FIG. 9 shows a percentage of compounds wherein their inhibition rates are over 75% is approximately 3.8% to the total number of all test substances in a prior method. FIG. 10 shows a percentage of compounds wherein their inhibition rates are over 40% is approximately 3.2% to the total number of all test substances in a prior method. Therefore, it is easy to select lead compounds in a pre-incubation assay because a number of pseudo-positive data decreases whereas it is difficult to select lead compounds in a prior method because a number of compounds showing positive date is large.

Figure 6:
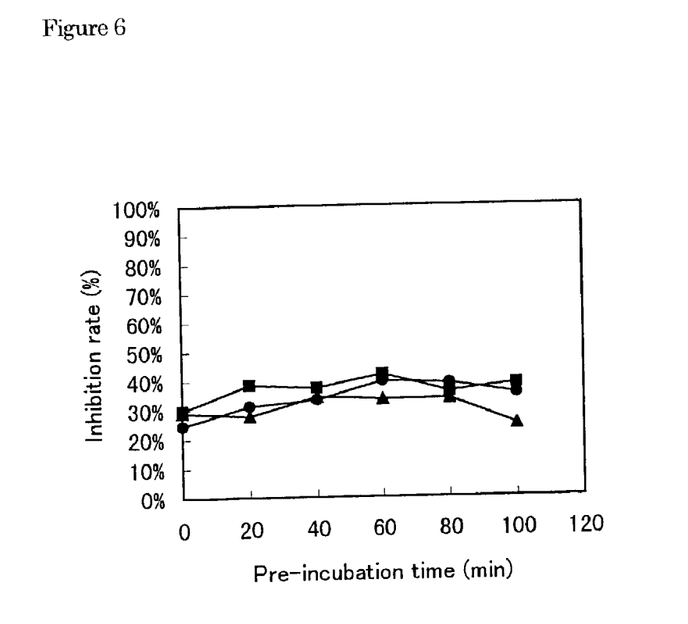
FIG. 6 shows a relationship between an inhibitory activity of 3'-dUTP to HCV RNA-dependent RNA polymerase and a pre-incubation temperature. In the figure, ● is used when a pre-incubation temperature is 25° C., ■ is used when a pre-incubation temperature is 20° C. and ▼ is used when a pre-incubation temperature is 2° C.
Figure 7:
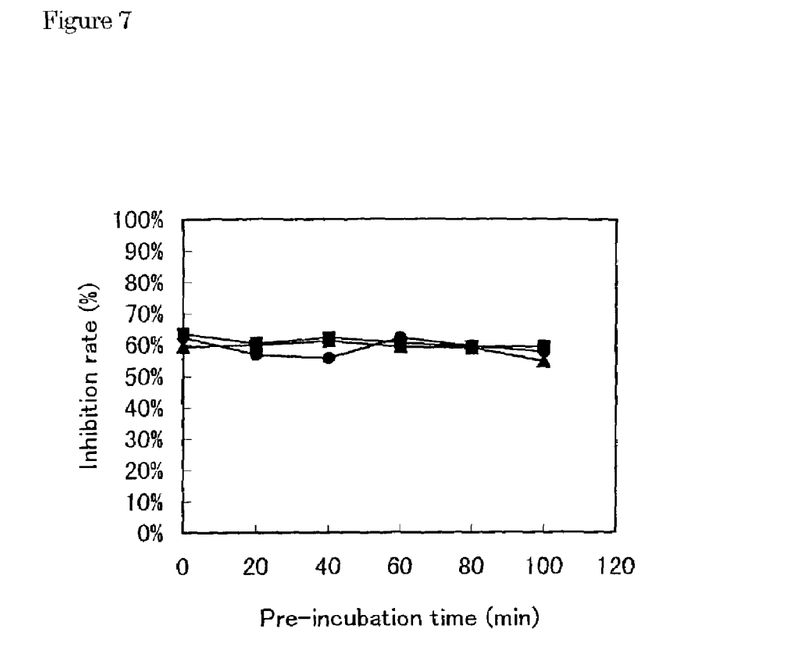
FIG. 7 shows a relationship between an inhibitory activity of Compound I-1 to HCV RNA-dependent RNA polymerase and a pre-incubation temperature. In the figure, ● is used when a pre-incubation temperature is 25° C., ● is used when a pre-incubation temperature is 20° C. and ▼ is used when a pre-incubation temperature is 2° C.
Figure 8:
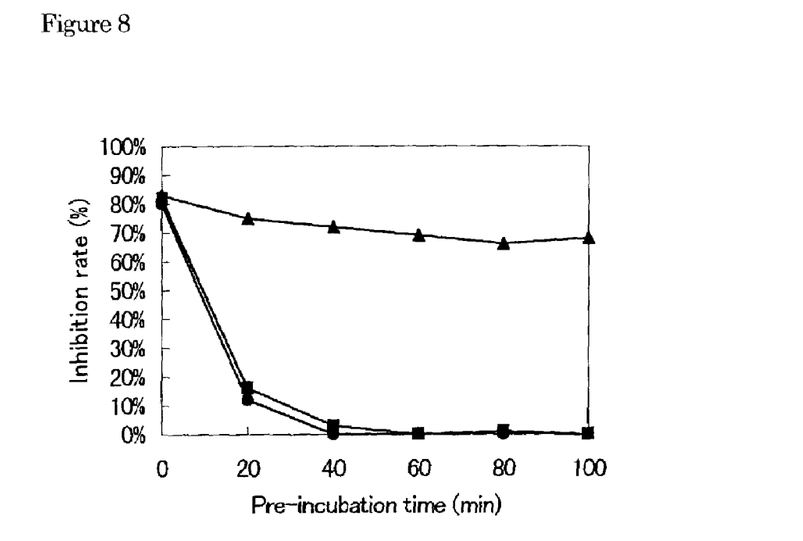
FIG. 8 shows a relationship between an inhibitory activity of Compound C to HCV RNA-dependent RNA polymerase and a pre-incubation temperature. In the figure, ● is used when a pre-incubation temperature is 25° C., ■ is used when a pre-incubation temperature is 20° C. and ▼ is used when a pre-incubation temperature is 2° C.

Lead compounds can effectively be found through a pre-incubation assay method of the present invention. Results obtained by using compounds obtained through the above screening are shown as examples. FIG. 6 shows a result obtained by using a positive control compound (3'-dUTP). FIG. 7 shows a result obtained by using Compound I-1 which was effectively found in a pre-incubation assay method. FIG. 8 shows a result obtained by using Compound C. The structure of Compound I-1 is shown below.

Compound I-1

Compound I-1 can be selected as an effective lead compound because it shows a positive result in a pre-incubation method as well as a positive control compound (3'-dUTP).

On the other hand, Compound C showing a positive result in a prior method can be excluded from candidates of lead compounds because it shows a negative result in a pre-incubation method.

FIG. 8 shows the effect of the pre-incubation is not found at a pre-incubation temperature of 2° C. Preferred as a pre-incubation temperature is 20 to 30° C.

Compound I-1 was selected as a lead compound as shown above and structurally close compounds (compounds of the formula: A—C(=O)—CH=C(OH)—COOH wherein A is an organic residue) were prepared. Inhibition activities of them to HCV RNA-dependent RNA polymerase were examined in accordance with a manner described in the following Example 1. The results are shown in the following Table 1. A compound of the formula: A—C(=O)—CH=C(OH)—COOH can form a structure of the formula: A—CH(OH)=CH—C(=O)—COOH or of the formula: A—C(=O)—CH$_2$—C(=O)—COOH, wherein A is an organic residue. A compound of any structure is within the scope of the present invention.

TABLE 1

Inhibition activities of compounds of the formula:
A—C(=O)—CH=C(OH)—COOH
to HCV RNA-dependent RNA polymerase

| Comp. No. | Group of the formula: —A | Inhibition rate at a concentration of 100 μg/ml (%) | IC$_{50}$ (μg/ml) |
|---|---|---|---|
| I-1 | 3-hydroxyphenyl | >99 | 0.4 |
| I-2 | 4-hydroxyphenyl | 99 | 0.9 |
| I-3 | 4-methylphenyl | 99 | 1.0 |
| I-4 | 4-aminophenyl | >99 | 1.4 |
| I-5 | phenyl | 98 | 2.3 |
| I-6 | 5-meyhylthiophen-2-yl | 97 | 3.1 |
| I-7 | naphthalen-2-yl | 95 | 6.9 |
| I-8 | indol-2-yl | 95 | 6.9 |
| I-9 | 4-chlorophenyl | 94 | 7.1 |
| I-10 | thiophen-3-yl | 94 | 7.2 |
| I-11 | 4-fluorophenyl | 94 | 7.4 |
| I-12 | 3-methoxyphenyl | 94 | 8.4 |
| I-13 | thiophen-2-yl | 92 | 8.7 |
| I-14 | 3-bromophenyl | 93 | 8.9 |
| I-15 | 1-methylpyrrol-2-yl | 94 | 9.8 |
| I-16 | pyrrol-2-yl | 92 | 10 |
| I-17 | 4-hydroxy-3-methoxyphenyl | 92 | 11 |
| I-18 | 2,4-dichlorophenyl | 90 | 13 |

An activator or an inhibitor to an enzyme can effectively be found in the present assay method. A compound of the formula: A—C(=O)—CH=C(OH)—COOH wherein A is an organic residue has an inhibition activity to a HCV RNA-dependent RNA polymerase and is useful as an agent for treating hepatitis C. The above result shows an organic residue in A is not limited to the specific residue and the structure of the formula: —C(=O)—CH=C(OH)—COOH is important for exhibiting a inhibition activity to a HCV RNA-dependent RNA polymerase.

A HCV RNA-dependent RNA polymerase can be inhibited by contacting a compound obtained through an assay of the present invention and a HCV RNA-dependent RNA polymerase. A replication of HCV can be inhibited by contacting a compound obtained through an assay of the present invention and HCV.

EXAMPLE

Preparation of HCV RNA-dependent RNA Polymerase

A cDNA encoding HCV RNA-dependent RNA polymerase was made by use of HCV positive human plasma and HCV RNA-dependent RNA polymerase was expressed using the insect cells or the E. coli. HCV RNA-dependent RNA polymerase in the cell extract was purified by use of an anion exchange chromatography, a heparin affinity chromatography, a polyU affinity chromatography, a cation exchange chromatography and gel filtration chromatography. The purification was performed at 4° C. and Tris buffer (pH 7.5) containing ethylenediaminetetraacetic acid (1 mM), dithiothreitol (10 mM) and glycerol (20%) was used. The enzyme purified was stored at 4° C. until use for the assays.

Example 1

The Assay Method with Pre-incubation Using HCV RNA-Dependent RNA Polymerase

1) The buffer I [1] (10.5 μl) containing Tris-HCl (100 mM, pH 7.5), MgCl$_2$ (25 mM), dithiothreitol (5 mM), KCl (125 mM) and ethylenediaminetetraacetic acid (5 mM) was transferred to a polypropylene tube and then poly(A)[2] solution (100 μg/ml, 10.5 μl), oligo(U)$_{12}$ [3] solution (1 μg/ml, 10.5 μl) and water (8 μl) were added into the tube and mixed.

2) Next, HCV RNA-dependent RNA polymerase (10.5 μl) was added into the tube and pre-incubated at 25° C. for 60 ml.

3) The enzyme solution pre-incubated (50 μl) was added to a test compound (5.26 μl/well) dissolved with dimethyl sulfoxide or water in a well of a 96-wells microtiter plate.

4) Additionally, the buffer II (10.6 μl) containing Tris-HCl (100 mM, pH 7.5), MgCl$_2$ (25 mM), dithiothreitol (5 mM), KCl (125 mM), ethylenediaminetetraacetic acid (5 mM) and UTP 4) (2.1 μM, 1 μCi $^3$H-UTP), was mixed with water (39.4 μl). The mixture (50 μl) was added into the well and mix, and then the enzyme reaction was performed at 25° C. for 30 min.

5) After enzyme reaction for 30 min, the enzyme reaction was stopped by adding disodium ethylenediaminetetraacetic acid (50 mM, 50 μl).

6) By use of the cell-harvester, all volume of the enzyme reaction sample was transferred onto a filtermat bound with diethylaminoethyl base (referred to as DEAE-filtermat) and washed twice for 10 sec with sodium phosphate buffer (0.25 M, pH 7.0) and once for 10 sec with deionized water.

7) The DEAE-filtermat was dried at 95° C. for 15 min and transferred into a sample bag with liquid scintillater (10 ml), and then a sample bag was sealed.
8) The radio activity was measured by a scintillation counter.
9) The inhibitory rate was calculated from the radioactivity measured (ccpm) as follows.

$$\text{Inhibitory rate} = 100 - (\text{ccpm with test compound} - \text{ccpm without enzyme}) \div (\text{ccpm without test compound} - \text{ccpm without enzyme}) \times 100$$

The concentration of compound at 50% inhibition ($IC_{50}$ value) was calculated from the compound concentration used and the inhibitory rate calculated.

When use of a compound at a μg/ml results in A % inhibition and use of a compound at β μg/ml results in B % inhibition on condition of A≧50>B the IC50 value is obtained by the calculation as follows.

$$IC_{50}\,(\mu g/ml) = 10^{[(50-B)/(A-B) \times (\log^\alpha - \log^\beta) + \log^\beta]}$$

1) All of water used as an experimental material from 1) to 5) was treated with diethyl pyrocarbonate to inactivate ribonuclease. As the treatment of diethyl pyrocarbonate, diethyl pyrocarbonate (0.1 g) was dissolved in de-ionized water (100 ml), incubated at 37° C. for 24 hr and then autoclaved at 120° C. for 30 min.
2) Poly(A) is a single strand polynucleotide consisted of adenylic acid only and used as template.
3) Oligo($U$)$_{12}$ is a single strand oligonucleotide consisted of 12 molecules of uridylic acid and used as primer.
4) UTP is uridine triphosphate and used as substrate.

When compound I-1, 3'-dUTP, compound A, compound B and compound C were used as test compounds, the inhibitory rates of the compounds for HCV RNA-dependent RNA polymerase were shown in Table 2. Concentrations of the compounds were as follows.

Compound I-1: 0.5 μg/ml
3'-dUTP: 0.7 μM
Compound A: 100 μg/ml
Compound B: 50 μg/ml
Compound C: 25 μg/ml

TABLE 2

| Compound No. (concentration) | Inhibitory rate |
|---|---|
| I-1 (0.5 μg/ml) | 62% |
| 3'-dUTP (0.7 μM) | 79% |
| A (100 μg/ml) | 19% |
| B (50 μg/ml) | 1% |
| C (25 μg/ml) | 2% |

Reference 1

The prior assay method using HCV RNA-dependent RNA polymerase
1) The buffer I [1] (10.5 μl) containing Tris-HCl (100 mM, pH 7.5), MgCl$_2$ (25 mM), dithiothreitol (5 mM), KCl (125 mM) and ethylenediaminetetraacetic acid (5 mM) was transferred to a polypropylene tube and then poly(A) [2] solution (100 μg/ml, 10.5 μl), oligo($U$)$_{12}$ [3] solution (1 μg/ml, 10.5 μl) and water (8 μl) were added into the tube. After mixing, the tube was cooled on ice.
2) Next, HCV RNA-dependent RNA polymerase (10.5 μl) cooled on ice was added into the tube and mixed.
3) The mixture cooled (50 μl) was added to a test compound (5.26 μl/well) dissolved with dimethyl sulfoxide or water in a well of a 96-wells microtiter plate.
4) Additionally, the buffer II (10.6 μl) containing Tris-HCl (100 mM, pH 7.5), MgCl$_2$ (25 mM), dithiothreitol (5 mM), KCl (125 mM), ethylenediaminetetraacetic acid (5 mM) and UTP [4] (2.1 μM, 1 μCi $^3$H-UTP), was mixed with water (39.4 μl). The mixture (50 μl) was added into the well and mix, and then the enzyme reaction was performed at 25° C. for 30 min.
5) After enzyme reaction for 30 min, the enzyme reaction was stopped by adding disodium ethylenediaminetetraacetic acid (50 mM, 50 μl).
6) By use of the cell-harvester, all volume of the enzyme reaction sample which was described in 5) was transferred onto a DEAE-filtermat and washed twice for 10 see with sodium phosphate buffer (0.25 M, pH 7.0) and once for 10 sec with de-ionized water.
7) The DEAE-filtermat was dried at 95° C. for 15 min and transferred into a sample bag with liquid scintillater (10 ml), and then a sample bag was sealed.
8) The radio activity was measured by a scintillation counter.
9) The inhibitory rate was calculated from the radioactivity measured (ccpm) as follows.

$$\text{Inhibitory rate} = 100 - (\text{ccpm with test compound} - \text{ccpm without enzyme}) \div (\text{ccpm without test compound} - \text{ccpm without enzyme}) \times 100$$

When compound I-1, 3'-dUTP, compound A, compound B and compound C were used as test compounds, the inhibitory rates of the compounds for HCV RNA-dependent RNA polymerase were shown in Table 3. Concentrations of the compounds were as follows.

Compound I-1: 0.5 μg/ml
3'-dUTP: 0.7 μM
Compound A: 100 μg/ml
Compound B: 50 μg/ml
Compound C: 25 μg/ml

TABLE 3

| Compound No. (concentration) | Inhibitory rate |
|---|---|
| I-1 (0.5 μg/ml) | 62% |
| 3'-dUTP (0.7 μM) | 68% |
| A (100 μg/ml) | 50% |
| B (50 μg/ml) | 63% |
| C (25 μg/ml) | 67% |

Examination 1

Effects of the pre-incubation that is a special feature of the assay method as the present invention were evaluated. In this specification, RdRp or HCV RdRp means HCV RNA-dependent RNA polymerase.

The mixture of the buffer I, poly(A), oligo(U)$_{12}$ and recombinant RdRp was pre-incubated for 0 min, 15 min, 30 min, 45 min, 60 min, 90 min, 120 min, 150 min and 180 min respectively, before the enzyme reaction at 25° C. for 30 min (FIG. 3). The solvent, DMSO or water was used instead of test compound solution.

Enzyme activity was estimated by determining $_3$H-UTP as substrate incorporated into the product. The enzyme activity increased with an increase in the pre-incubation time and leveled off after approximately 60 min. The increase of enzyme activity was appeared in both cases of DMSO and water as the solvent of compound. When DMSO and water was used, the enzyme with pre-incubation showed 2.7 times and 4.2 times respectively in the best case as active as that without pre-incubation.

From the above-mentioned findings, it was confirmed that increase of enzyme activity was brought about by pre-incubating the buffer I, poly(A), oligo(U) and recombinant RdRp before the enzyme reaction.

Examination 2

Next, effects of pre-incubation on thermostability of RdRp were determined.

Time course of HCV RdRp activity at 25° C. or 37° C., with or without pre-incubation was shown in FIG. 4. In the prior assay method without pre-incubation, the velocity of enzyme reaction at 37° C. was getting lower after the enzyme reaction for 20 min and the amount of the product in enzyme reaction for 60 min at 37° C. was about 50% less than that at 25° C. On the other hand, in the pre-incubation assay method, the velocity of enzyme reaction at 37° C. tended to decrease after the enzyme reaction for 20 min but the amount of the product in enzyme reaction increased and the amount of the product in enzyme reaction for 60 min at 37° C. was a higher value at about 125% as compared with that at 25° C.

These data showed that the pre-incubation of the buffer 1, poly(A), oligo(U) and recombinant RdRp resulted in increase of thermostability of RdRp during the enzyme reaction.

Examination 3

In the screening for HCV RNA-dependent RNA polymerase inhibitor, there is a dissociation of inhibitory effect as a different point between an assay method of the present invention and a prior assay method. Treatment of pre-incubation resulted in great decrease of inhibitory effect of many compounds. Therefore, the influence of pre-incubation on the inhibitory value of enzyme inhibitor was determined. Using several compounds which evaluated RdRp inhibition in the prior assay method, the time course of HCV RdRp inhibitory effect was determined for 0 min, 15 min, 30 min, 45 min, 60 min, 90 min, 120 min, 150 min and 180 min as a pre-incubation time (FIG. 5).

There was not a large influence by pre-incubation using 3'-dUTP as an analog of substrate UTP. However, when the other three compounds, compound A, compound B and compound C were used, the inhibitory effect decreased with increasing pre-incubation time and was stable in about 60 min of pre-incubation time.

These results showed that the treatment of pre-incubation of the buffer I, poly(A), oligo(U) and recombinant RdRp lead to great change of RdRp inhibitory effect by kinds of compounds.

Examination 4

Influence of pre-incubation on inhibitory value of enzyme inhibitor was determined in Examination 3. The temperature of pre-incubation in Examination 3 was changed and the time course of inhibitory effect was determined at variant temperature of pre-incubation.

Using several compounds, 3'-dUTP, compound I-1 and compound C, which evaluated RdRp inhibition in the prior assay method, the time course of HCV RdRp inhibitory effect was determined at 2° C., 20° C. and 25° C. as a pre-incubation temperature for 0 min, 20 min, 40 min, 60 min, 80 min, and 100 min as a pre-incubation time (FIG. 6, FIG. 7, FIG. 8). There was not influence by pre-incubation at any temperatures using 3'-dUTP as an analog of substrate UTP and compound I-1. However, when compound C was used, the inhibitory effect decreased greatly with increasing pre-incubation time at 20° C. and 25° C. but did not appear clear influence by pre-incubation at 2° C.

These results showed that the treatment of pre-incubation which lead to great change of RdRp inhibitory effect had variant influence by change of temperature.

Examination 5

To compare a pre-incubation assay method with the prior assay method, random screening assay was performed using several ten thousands compounds with different chemical structures each to each as test substances.

First, the compounds were mixed ten by ten. The concentration of each test compound mixed was adjusted to 0.83 µg/ml. The inhibitory rate was obtained according to the prior assay method described in Reference 1. The result is shown in FIG. 9. On the other hand, the compounds were mixed five by five. The concentration of each test compound mixed was adjusted to 49 µg/ml. The inhibitory rate was obtained according to a pre-incubation assay method of the present invention described in Example 1. The result is shown in FIG. 10.

Example 2

The assay method with pre-incubation using HCV RNA-dependent RNA polymerase without radioisotope-labeled substrate.

In Example 1, $^3$H-UTP, that is UTP labeled with tritium as radioisotope was used as substrate in the assay with pre-incubation using HCV RNA-dependent RNA polymerase. Herein, digoxigenin-labeled UTP (DIG-UTP) instead of $^3$H-UTP was used as substrate in the assay with pre-incubation using HCV RNA-dependent RNA polymerase.

1) Streptavidin (1 mg/ml) was dissolved in the phosphate buffer saline (PBS) containing NaCl (0.137 M), KCl (2.68 mM), potassium dihydrogenphosphate (1.47 mM) and sodium phosphate (8.06 mM).

2) The streptavidin solution was diluted 25-fold with the carbonate buffer containing sodium carbonate (0.9 M) and sodium hydrogencarbonate (0.1 M).

3) The 25-fold streptavidin solution (50 μl/well) was transferred to a well of 96 wells-microtiter palate with flat bottom for immunoassay and then the plate was kept at 4° C. over night.
4) After the 96 wells-microtiter plate was coated with streptavidin, the well was washed twice by adding, mixing and draining PBS (200 μl/well).
5) The skim milk dissolved with PBS (1%, 300 μl) was transferred into each well and was kept at room temperature for 30 min.
6) After the plate was washed once with PBS (200 μl/well), the well was filled with PBS (300 μl/well) and then the plate was stored at 4° C.
7) After the PBS was drained from the streptavidin-coated plate stored under the condition described in 6), the well was washed once with PBS (200 μl/well) and was filled with de-ionized water (300 μl/well).
8) The buffer I (10 μl) containing Tris-HCl (100 mM, pH 7.5), $MgCl_2$ (25 mM), dithiothreitol (5 mM), KCl (125 mM) and ethylenediaminetetraacetic acid (5 mM) was transferred to a polypropylene tube and then poly(A) solution (6.25 μg/ml, 10 μl), biotin-labeled oligo$(U)_{12}$ solution (3 μg/ml, 10 μl), water (10 μl) and HCV RNA-dependent RNA polymerase solution (10 μl) were added into the tube and mixed calmly.
9) De-ionized water was drained from the plate described in 7), and the solution (50 μl/well) at once after the mixing described in 8) was transferred to each well. After mixing by a plate mixer, the solution was pre-incubated at 25° C. for 1 hr.
10) On the other hand, the buffer I (10 μl) was transferred into another tube, and UTP (1 μM, 10 μl), DIG-UTP (300 μM, 1 μl), water (24 μl) and a test compound dissolved with dimethyl sulfoxide or water (5 μl) were added to the tube and mixed calmly. Concentrations of the compounds used were as follows.

| | |
|---|---|
| Compound (I-1): | 0.5 μg/ml |
| 3'-dUTP: | 0.7 μM |
| Compound A: | 100 μg/ml |
| Compound B: | 50 μg/ml |
| Compound C: | 25 μg/ml |

11) The mixed solution (50 μl/well) described in 10) was transferred into each well after the pre-incubation described in 9), mixed by a plate mixer and then incubated at 25° C. for 1 hr.
12) When the enzyme reaction was in 1 hr, the enzyme reaction was stopped by adding ethylenediaminetetraacetic acid (0.1 M, 50 μl/well).
13) The plate was washed twice with PBS (200 μl/well) after end of the enzyme reaction.
14) Next, alkaline phosphatase-labeled anti-DIG antibody (3 U/ml, 100 μl/well) diluted 250-fold with PBS containing skim milk (0.5%) was transferred each well. After mixing by a plate mixer, immuno-reaction was performed at 25° C. for 1 hr.
15) Each well was washed twice with PBS (200 μl/well) containing skim milk (0.05%) and then washed twice with PBS (200 μl/well).
16) Substrate solution (150 μl/well) for alkaline phosphatase was prepared by mixing of Tris-HCl (100 mM, pH 9.5), NaCl (100 mM), $MgCl_2$ (5 mM) and p-nitrophenyl phosphate (6 mM) just before use. The substrate solution was transferred into each well of the plate, mixed by a plate mixer and then incubated at 25° C. for 1 hr until the color appears in the solution.
17) The plate was set on a plate reader and the absorbance was measured at 405 nm.
18) The inhibitory rate was calculated from the optical density (unit; OD) measured as follows.

Inhibitory rate = 100 − (OD with test compound −

OD without enzyme) ÷

(OD without test compound −

OD without enzyme) × 100

Table 4 summarized the comparison between inhibitory rates in the assay with the pre-incubation and those in the assay without the pre-incubation.

TABLE 4

| | Inhibitory rate Treatment of pre-incubation | |
|---|---|---|
| Compound No. (concentration) | + | − |
| I-1 (0.5 μg/ml) | 52% | 59% |
| 3'-dUTP (0.7 μM) | 50% | 44% |
| A (100 μg/ml) | 24% | 87% |
| B (50 μg/ml) | 20% | 28% |
| C (25 μg/ml) | 15% | 87% |

INDUSTRIAL APPLICABILITY

The pre-incubation assay method can heighten 1) an activity to an enzyme and 2) thermostability and reduce 3) pseudo-positive data.

The invention claimed is:

1. A method for assaying for an inhibitor to a virus RNA-dependent RNA polymerase which comprises:
    (a) incubating a solution comprising said polymerase, a template RNA, a primer RNA and a metal ion in the absence of both a test substance and a substrate of said polymerase for 15 minutes or more at 20 to 40° C., and
    (b) mixing a test substance and a substrate of said polymerase with said incubated solution.
2. The method according to claim 1 which comprises:
    (a) incubating the solution comprising said polymerase, the template RNA, the primer RNA and the metal ion in the absence of both the test substance and the substrate of said polymerase, and
    (b) comparing a virus RNA-dependent RNA polymerase activity measured by mixing the test substance and the substrate of said polymerase with said incubated solution and reacting said polymerase with said substrate of said polymerase, with a virus RNA-dependent RNA polymerase activity measured by mixing only the substrate of said polymerase with said incubated solution and reacting said polymerase with said substrate of said polymerase.
3. The method according to claim 1 wherein said template RNA is poly(A), said primer RNA is oligo(U), said metal ion is $Mg^{2+}$ and said substrate of said polymerase is $^3$H-UTP or $^{32}$P-UTP.

* * * * *